United States Patent [19]

Crosby, Jr.

[11] 4,064,740

[45] Dec. 27, 1977

[54] APPARATUS AND METHOD FOR MEASURING PERMEABILITY

[75] Inventor: Edward Lewis Crosby, Jr., Indialantic, Fla.

[73] Assignee: RCA Corporation, New York, N.Y.

[21] Appl. No.: 734,728

[22] Filed: Oct. 22, 1976

[51] Int. Cl.² ............................................. G01M 3/26
[52] U.S. Cl. ...................................................... 73/38
[58] Field of Search ...................... 73/38, 40, 45, 45.1, 73/45.2

[56] References Cited

U.S. PATENT DOCUMENTS 2,021,948  11/1935  Schopper ................................. 73/38

FOREIGN PATENT DOCUMENTS 835,231  8/1955  United Kingdom ..................... 73/40

Primary Examiner—S. Clement Swisher
Attorney, Agent, or Firm—H. Christoffersen; Samuel Cohen; William Squire

[57] ABSTRACT

A material whose permeability to a fluid, such as a gas, is to be measured, forms at least part of the wall of a chamber which is otherwise impervious to the fluid, and the fluid is located within the chamber at a reference pressure level. In one embodiment, after a given interval of time, sufficient fluid is returned to the chamber to restore the pressure to its reference level. The volume of fluid required is a measure of the permeability of the material.

9 Claims, 1 Drawing Figure

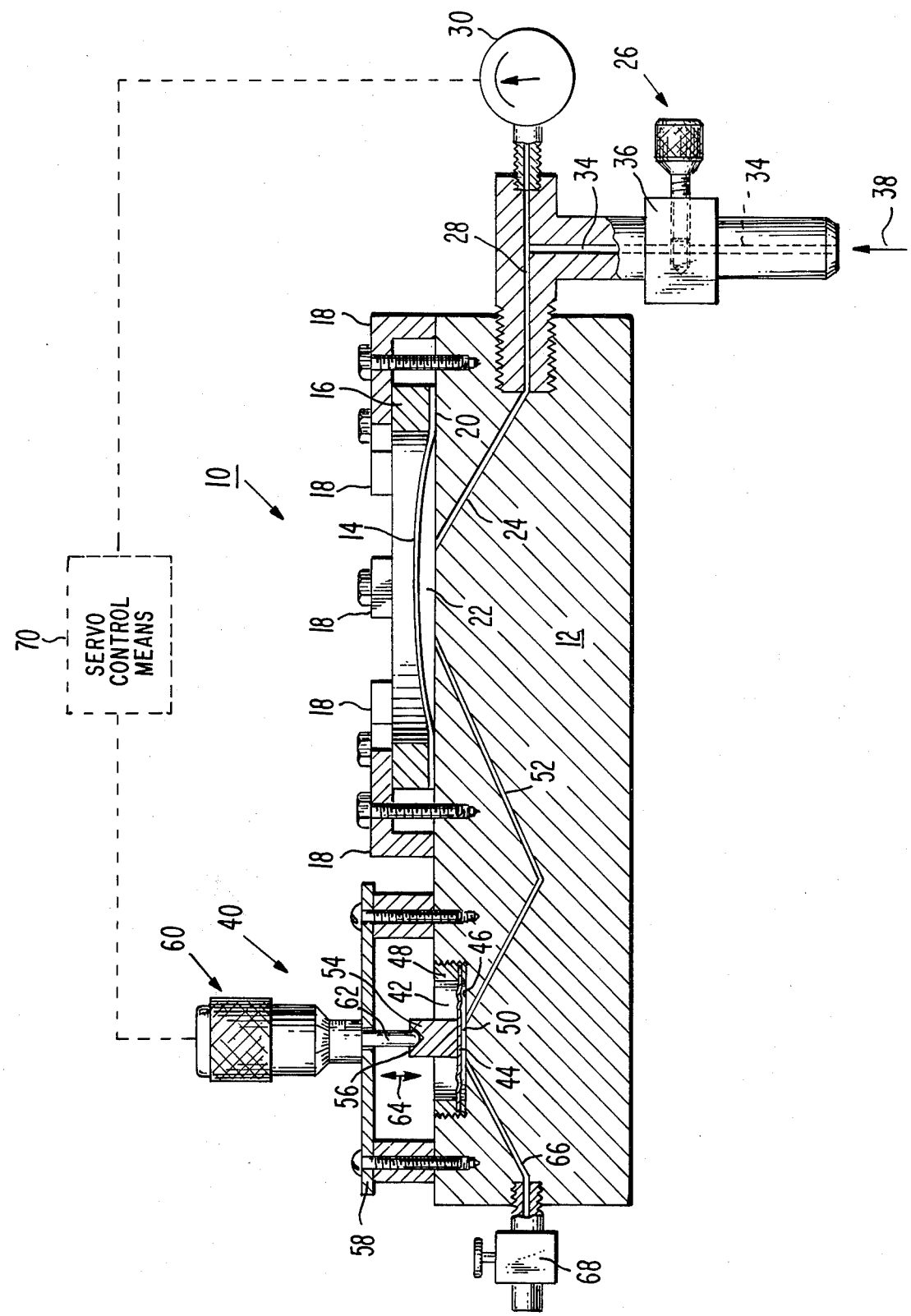

APPARATUS AND METHOD FOR MEASURING PERMEABILITY

The present invention relates to a method and apparatus for determining the permeability of a material.

It is important in the construction of balloons, blimps, inflated buildings, gas tank liners and so on, that the fabric employed be capable of retaining the fluid-a gas in these examples, for a long period of time. Apparatus presently in common use for testing the permeability of these and other kinds of fabric often are inadequate to measure very low permeabilities or to compare small differences in permeability of two fabrics.

One widely used instrument for measuring permeability known as the "Cambridge permeameter", is described in United States Government specification Federal Test Method Standard No. 191, Textiles, Method 5460 Permeability to Hydrogen Gas, Cloth. In operation, the test gas is admitted to one chamber and the concentration of that portion of the gas which diffuses through the test piece into a second chamber is measured as a function of time. A volumetric bridge which is sensitive to thermal conductivity of the gas/air mixture in the second chamber is employed to make the measurement. A thermal conductivity sensor such as katharometer or semiconductor element may be used. In fabrics of interest, the rate of diffusion of the gas may be so small that the bridge is relatively insensitive thereto—it barely becomes unbalanced. For example, a fabric meeting the specification that the "permeability be not greater than one liter per square meter per day," which is typical of a balloon fabric, would cause a deflection on a Cambridge indicator of only a fraction of one scale division.

The present invention is directed to a test apparatus for meeting the need discussed above.

The sole FIGURE of the drawing is a sectional view of an apparatus embodying the present invention.

In the drawing, apparatus 10 includes a suitable base 12 made of metal or other material essentially impermeable to the test gas. The material 14 whose permeability is being tested is formed into a circular disc. The peripheral edge portion of material 14 is coated with a combination of petroleum jelly and bees wax to seal the peripheral areas of material 14 from permeation by the test gas. The jelly and wax coating defines a circular, centrally disposed uncoated permeability test area of reference size, i.e., 0.01 square meter, and serves also to make the seal between annular ring 16 and base 12 gas-tight when the fabric 14 is in place between the two, as shown.

The ring 16 is secured to base 12 by a plurality of spaced L-shaped clamps 18 clamping the material 14 to the upper surface 20 of base 12 with the test area within the ring and with a space 22 between the material 14 and the surface 20. A fluid passage 24 disposed in base 12 opens at one end at space 22 and at the other end at a fluid connector and microvalve assembly 26. Assembly 26 is threaded to base 12 and includes a passage 28 in fluid communication with passage 24. A pressure gauge 30 is coupled to passage 28. Test gas inlet nozzle 32 has a test gas passage 34 in fluid communication with passage 28 via microvalve 36. Microvalve 36 serves to open and close the passage 34. The test gas is applied to nozzle 32 in the direction 38. The test gas applied to space 22 has a pressure preferably in the range of about one-half inch to six inches of water gauge. Thus, the pressure of the gas in volume 22 is only slightly above atmospheric pressure. The exact value is not critical so long as it exceeds atmospheric pressure.

Gauge 30 is a sensitive instrument provided to detect minute changes in pressure of the test gas in space 22, the gauge 30 continuously monitoring the test pressure. In one embodiment, the pressure gauge may consist of a bellows driving the movable element of an inductive linear position transducer. The transducer output, linear with gas pressure on the bellows, is read-out on a voltmeter, which may be calibrated directly in units of pressure. A sensitive, easily expanded cylindrical, multi-section bellows, having good retrace characteristic, is ported into the gas space of the instrument. The outside of the bellows drives the free core of a linear variable differential transformer (LVDT). This LVDT sensitivity converts the core position to a d-c voltage analog by being responsive to the magnetic coupling of two internal coils. The a-c signal for the primary coil (as well as the synchronous detector which provides d-c output) and accessory circuits are within the LVDT housing. The bellows drives the core with a fine steel wire so as to accomodate misalignment of the core axis and the bellows thrust vector. Friction is reduced essentially to zero by operating the gauge in a vertical position. The output of the LVDT is read-out on a digital voltmeter, (which could be calibrated to read pressure directly).

Microvalve 36 is a device which provides minute adjustment of gas flow which is used to accurately adjust gas pressure in the assembly in the range given above. Both gauge 30 and valve 36 are conventional, commercially available devices.

Disposed on base 12 is volume measuring assembly 40. It includes circular cavity 42 formed in surface 20. Disposed in cavity 42 is a thin flexible gas impermeable membrane 44. Membrane 44 can be, for example, a 5 mil thick circular disc of corrugated stainless steel such as used in a conventional aneroid chamber. Membrane 44 is clamped to the cavity 42 base surface 46 by a clamping ring 48 threaded into cavity 42 and sealed to the surface 46 with a gas impermeable adhesive. One end of passage 52 is in fluid communication with the space 50 formed by membrane 44 with base surface 46. The other end of passage 52 is in fluid communication with space 22. Secured to and disposed on the upper outer surface of membrane 44 is a bushing 54 having a conical concave seat 56 facing upwardly away from base 12. Secured to base 12 by a suitable support structure 58 is a conventional micrometer assembly 60. Assembly 60 has a micrometer spindle 62 with a spherical tip which engages conical seat 56. As well known in the machine tool art, micrometer assembly 60 can measure displacements to the accuracy of 0.0001 inches in the direction 64. As is already apparent, displacement of spindle 62 in direction 64 toward base 12 flexes membrane 44 in that direction decreasing the volume of space 50. The natural spring pressure of membrane 44 permits the volume of space 50 to increase when the spindle 62 is moved away from base 12, it being understood that membrane 44, in its initial condition, is slightly biased toward surface 46. In fluid communication with space 50 is a passage 66 which is selectively opened to the ambient via dump valve 68.

In operation, a circular disc of test material 14 initially is placed in the test apparatus, in the manner already described. The disc may be six inches in diameter and the fabric may include as an example an inner ply of 3 ½ ounce polyester cloth, an outer ply of 1.4 ounce of polyester cloth and coating of polyurethane over the inner and outer plys, and a butyl rubber coating at the interface of the two plys. This material can have a weight, for example, of 10 ounces per square yard. It may be that the permeability of the material should not exceed 1 liter per square meter, per day (24 hours) for balloon applications.

Micrometer valve 36 and dump valve 68 are placed in the open valve condition and a purge test gas with a pressure just sufficient to sweep out all contaminating gases is applied in direction 38 to nozzle 32. The test gas in the exemplary embodiment is helium. However, any gas may be used without altering the calibration. The gas may be passed through the system exiting to the ambient through dump valve 68, for a period of 5 minutes. Valve 36 is then closed followed by the closing of valve 68.

Pressure is read on gauge 30. The time of the pressure reading is noted. The pressure may be in the range noted above, that is, ¼ to 6 inches of water gauge, and conveniently, one inch of water gauge. The test time period may be of any suitable length and preferably is one-half hour for good balloon material. At the end of the half hour period, the pressure on gauge 30 is read. Any decrease in pressure is due to permeation of the test gas from space 22 to the ambient through test material 14.

Micrometer spindle 62 is translated in a manner to reduce the volume of space 50 by flexing membrane 44 toward base surface 46. Spindle 62 is displaced until the pressure at gauge 30 reads the same as the original pressure. The difference in micrometer readings measuring the linear displacements of spindle 62 in direction 64 is calibrated to provide a direct reading of the permeability of the material 14 in terms of liters per square meter per day. This instrument is accurate, repeatable, is simple to use and can be quickly set up for a given test.

To ensure that the membrane 44 displaces accurately in direction 64, the bushing 54 is secured to membrane 44 by welding or the like. The actual direction that membrane 44 displaces is not critical. But, membrane 44 should be displaced substantially in the same direction each time the spindle 62 is displaced to provide repeatability and accuracy.

It is important that the temperature of the unit remain stable during the test. As is well known, the coefficient of thermal expansion of gases is large so that relatively large volume changes will occur in the gas with slight temperature changes. Preferably the temperature of the test gas should remain within ±1° C. To thus maintain the temperature it is important that the adjustment of the valves 68 and 36 be made gradually so that there is no sudden expansion of the test gas through the valve. Such expansion may produce undesirable temporary temperature changes which may affect the test results.

While a single membrane 44 is shown in the drawing, it will be apparent that alternate arrangements for the volume measuring assembly 40 may be provided. For example, one such arrangement may include an aneroid chamber comprising two members such as members 44 sealed at the periphery thereof in a conventional manner. The aneroid chamber thus constructed has one aperature in fluid communication with a dump valve, such as valve 68 and a second aperture in fluid communication with the space 22 such as provided by passage 52 in the drawing. A suitable micrometer assembly such as assembly 60 is then disposed to displace one member of the aneroid chamber with respect to the other. It will occur to those skilled in the art that still other means for providing accurate volumetric displacement and measuring chambers may be provided for use in conjunction with the space 22 in the manner described above.

In the embodiment illustrated, the bellows chamber formed by member 44 is calibrated in fractional cubic centimeters per one thousandth inch thrust of the micrometer spindle 62. That is, each 0.001 inch displacement of spindle 62 represents a given volume change of space 50. The test material 14 having an area 0.01 square meters in combination with the calibration of the micrometer spindle can be converted to "liters per square meter per day" by a simple arithmetic computation.

During the purge procedure, certain factors should be considered. The gauge pressure should be kept as close as possible to the desired test pressure during the purge, especially with low modulus elastic test materials, to avoid "stretch" and "relaxation" effects. If the purge pressure is too high, the test material may gradually relax during the test, thus increasing pressure and resulting in permeability which is lower than actual. On the other hand, if the purge pressure is too low, the material under test may gradually stretch, reducing test pressure and resulting in a pressure reading higher than actual.

A variation of the test procedure is to continually maintain the micrometer assembly 60 adjustment such that the initial test pressure continuously is indicated on meter 30. Such adjustment may be accomplished by a servo system 70 which monitors the pressure sensed by meter 30 and which drives the micrometer assembly 60 in a sense to maintain that pressure constant. All of this is shown schematically, in phantom, in the figure: In more detail, the pressure may be sensed by an electronic pressure readout system which produces an output voltage indicative of the pressure. Further, the micrometer spindle 62 may be coupled to an electronic position indicator to provide a direct digital reading of the actual travel of the spindle 62 and thus provide a digital output signal giving the permeability of the test material 14 in a direct, real-time reading.

To minimize stretch and relaxation effects of the test material 14, a stiff but porous lid (not shown) shaped to conform to the material may be placed over the material and secured, for example, to the inner surface of the ring 16. Such a lid could include a porous bronze disc covered by a perforated steel grid.

It is to be understood that the volume of space 22 is exaggerated in the drawing and the curvature of material 14 is also exaggerated. In fact, the material 14 is substantially flush against surface 20 of base 12. Thus, the lid described above would maintain this flush condition of the material 14 against surface 20.

The clamping arrangement provided by ring 16 and clamp 18 are illustrative. An alternative clamping ring may be provided similar to ring 48 and a corresponding cavity such as cavity 42 of the volume measuring assembly 40. With such a ring threaded directly to base 12 uniform and high clamping pressures may be provided ensuring a gas tight seal between material 14 and surface 20.

What is claimed is:

1. An apparatus for measuring the permeability of a material to a gas comprising:
   support means impermeable to said gas;
   clamp means for clamping said material to said support means and forming a test chamber between said material and said support means;

means in fluid communication with said test chamber for filling said chamber with said gas at a given test pressure value which tends to decrease, with time, to a lower test pressure value as said gas passes through said material;

diaphragm means in fluid communication with said test chamber secured to said support means and forming a chamber therebetween for supplying sufficient gas to said test chamber for returning the pressure therein to said given value and including means connected to said support means for displacing said diaphragm means to thereby alter the volume of said last-mentioned chamber; and means for indicating the volume of gas required to return said pressure within said chamber to said given value, said volume and the time during which the gas is permitted to pass through said material being indicative of the permeability, as a function of time, of said material.

2. The apparatus according to claim 1, wherein said clamp means includes a relatively flat member with an opening therein, the material being clamped between one surface of said member and a surface of said support and said chamber comprising as one wall thereof the region of the base within said opening and as another wall thereof the material opposite said region.

3. The apparatus of claim 1, wherein said means for displacing includes indicating means coupled thereto for indicating said difference in pressure values.

4. The apparatus of claim 1, wherein said means for filling said chamber includes passage means disposed in said support means for supplying said gas applied to an input thereto to said test chamber.

5. The apparatus of claim 1, further including fluid passage means disposed in said support means coupled in fluid communication with (a) said test chamber and said gas supplying means (b) said gas supplying means and the ambient, and (c) said test chamber and said test chamber filling means, and valve means arranged to selectively decouple said fluid passage means between (a) said gas supplying means and the ambient and (b) said test chamber and said test chamber filling means.

6. The apparatus of claim 1, wherein said test chamber filling means includes means for providing said gas to said test chamber at that pressure such that the test chamber pressure and the ambient pressure are substantially the same in value.

7. A method of measuring the permeability of a material to a gas comprising:

forming a first chamber at least a reference area of the wall of which is formed of said material and the remainder of which is impervious to said gas;

providing a reference chamber impervious to said gas in gas communication with said first chamber, to form a system comprising the two chambers in communication with one another;

filling said system, comprising said reference and first chambers, with a gas and when a reference pressure has been reached, closing said system, whereby said gas permeates through said material, and the pressure of the gas within said system tends to reduce as a function of time; and decreasing the reference chamber volume by an amount to increase the pressure of said gas to said given pressure by the end of a reference period of time, the size of the test area, the length of the reference period of time, and the decrease in the reference chamber volume together being indicative of the permeability of said material.

8. An apparatus for measuring the permeability of a material to a gas comprising:

support means impermeable to said gas;

clamp means for clamping said material to said support means and forming a test chamber between said material and said support means;

means in fluid communication with said test chamber for filling said chamber with said gas at a given test pressure value which tends to decrease, with time, to a lower test pressure value as said gas passes through said material;

means in fluid communication with said test chamber for supplying sufficient gas to said test chamber for returning the pressure therein to said given value including a membrane member adapted to flex in a given direction and sealed at the periphery thereof to said support means forming a chamber with said support means, said gas supplying means further including adjustment device means secured to said support means oriented to flex said member in said given direction; and means for indicating the volume of gas required to return said pressure within said chamber to said given value, said volume and the time during which the gas is permitted to pass through said material being indicative of the permeability, as a function of time, of said material.

9. An apparatus for measuring the permeability of a material to a gas comprising:

support means impermeable to said gas;

clamp means for clamping said material to said support means and forming a test chamber between said material and said support means;

means in fluid communication with said test chamber for filling said chamber with said gas at a given test pressure value which tends to decrease, with time, to a lower test pressure value as said gas passes through said material;

means comprising an aneroid chamber in fluid communication with said test chamber for supplying sufficient gas to said test chamber for returning the pressure therein to said given value, said means for supplying gas further including calibrated adjustment means for altering the volume of said aneroid chamber; and means for indicating the volume of gas required to return said pressure within said chamber to said given value, said volume and the time during which the gas is permitted to pass through said material being indicative of the permeability, as a function of time, of said material.

* * * * *